United States Patent
Callahan et al.

(10) Patent No.: US 11,242,518 B2
(45) Date of Patent: Feb. 8, 2022

(54) METHODS FOR CO-ISOLATION OF NUCLEIC ACIDS AND PROTEINS

(71) Applicant: Qiagen Sciences LLC, Germantown, MD (US)

(72) Inventors: Heather Callahan, San Diego, CA (US); Eddie Adams, San Diego, CA (US); Mark N. Brolaski, Encinitas, CA (US); Victoria Nieciecki, Vista, CA (US)

(73) Assignee: QIAGEN Sciences, LLP, Germantown, MD (US)

( * ) Notice: Subject to any disclaimer, the term of this patent is extended or adjusted under 35 U.S.C. 154(b) by 0 days.

(21) Appl. No.: 15/757,330

(22) PCT Filed: Sep. 2, 2016

(86) PCT No.: PCT/US2016/050197
§ 371 (c)(1),
(2) Date: Mar. 2, 2018

(87) PCT Pub. No.: WO2017/040992
PCT Pub. Date: Mar. 9, 2017

(65) Prior Publication Data
US 2019/0071665 A1 Mar. 7, 2019

Related U.S. Application Data

(60) Provisional application No. 62/214,877, filed on Sep. 4, 2015.

(51) Int. Cl.
| | | |
|---|---|---|
| C12N 15/10 | (2006.01) | |
| C07H 21/02 | (2006.01) | |
| C07H 1/06 | (2006.01) | |
| G01N 30/88 | (2006.01) | |
| G01N 30/00 | (2006.01) | |

(52) U.S. Cl.
CPC .......... *C12N 15/1013* (2013.01); *C07H 1/06* (2013.01); *C07H 21/02* (2013.01); *G01N 30/88* (2013.01); *G01N 2030/009* (2013.01); *G01N 2030/8831* (2013.01); *G01N 2030/8836* (2013.01)

(58) Field of Classification Search
CPC ....... C12N 15/1013; C07H 1/06; C07H 21/02
See application file for complete search history.

(56) References Cited

U.S. PATENT DOCUMENTS

| | | | |
|---|---|---|---|
| 4,748,234 A | 5/1988 | Dorin et al. | |
| 4,843,155 A * | 6/1989 | Chomczynski | .... C12N 15/1003 536/25.41 |
| 5,081,010 A | 1/1992 | Cummins et al. | |
| 5,342,931 A | 8/1994 | Woodard et al. | |
| 5,391,497 A | 2/1995 | Menon et al. | |
| 5,637,687 A | 6/1997 | Wiggins | |
| 5,648,225 A | 7/1997 | Kim et al. | |
| 5,665,359 A | 9/1997 | Ho et al. | |
| 5,705,628 A | 1/1998 | Hawkins | |
| 5,777,098 A | 7/1998 | Gray et al. | |
| 5,834,282 A | 11/1998 | Habuchi et al. | |
| 5,898,071 A | 4/1999 | Hawkins | |
| 5,922,328 A | 7/1999 | Spector et al. | |
| 6,534,262 B1 | 3/2003 | McKernan et al. | |
| 6,579,697 B1 | 6/2003 | Wallach et al. | |
| 7,074,916 B2 | 7/2006 | Bastian et al. | |
| 7,429,648 B1 | 9/2008 | Wallach et al. | |
| 7,459,548 B2 | 12/2008 | Brolaski et al. | |
| 8,399,218 B2 | 3/2013 | Gupta et al. | |
| 8,834,694 B2 | 9/2014 | Brolaski et al. | |
| 8,889,393 B2 | 11/2014 | Sjöblom et al. | |
| 9,051,563 B2 * | 6/2015 | Forman | ................. C07H 21/04 |
| 2003/0153083 A1 | 8/2003 | Shir et al. | |
| 2005/0059021 A1 | 3/2005 | Farid et al. | |
| 2007/0190535 A1 | 8/2007 | Hall, Jr. et al. | |
| 2007/0202511 A1 | 8/2007 | Chen et al. | |
| 2009/0048437 A1 | 2/2009 | Lee et al. | |
| 2009/0111159 A1 | 4/2009 | Brolaski et al. | |
| 2010/0093634 A1 | 4/2010 | Welling et al. | |
| 2010/0292316 A1 | 11/2010 | Sanders et al. | |
| 2010/0331534 A1 | 12/2010 | Khan et al. | |
| 2012/0271042 A1 | 10/2012 | Jiang et al. | |
| 2013/0164819 A1 | 6/2013 | Sjöblom et al. | |
| 2014/0051844 A1 | 2/2014 | Forman et al. | |
| 2014/0212868 A1 | 7/2014 | Wilmes et al. | |
| 2014/0288272 A1 | 9/2014 | Allison et al. | |
| 2015/0185126 A1 | 7/2015 | Callahan et al. | |
| 2017/0021333 A1 | 1/2017 | Kovacs et al. | |
| 2018/0245064 A1 | 8/2018 | Moroney et al. | |
| 2019/0071665 A1 | 3/2019 | Callahan et al. | |

FOREIGN PATENT DOCUMENTS

| | | |
|---|---|---|
| CN | 104152436 A | 11/2014 |
| EP | 2 199 295 A1 | 6/2010 |
| EP | 2 345 719 A1 | 7/2011 |

(Continued)

OTHER PUBLICATIONS

Likhite (Journal of Biomolecular Techniques 22:37-44, 2011).*
"Thermo Scientific Pierce Cell Lysis Technical Handbook," Version 2, 2009 (54 pages).
Braid et al., "Removal of PCR inhibitors from soil DNA by chemical flocculation," *Journal of Microbiological Methods* 52(3):389-393, 2003 (6 pages).
Chourey et al., "Direct Cellular Lysis/Protein Extraction Protocol for Soil Metaproteomics," *Journal of Proteome Research* 9(12):6615-6622, 2010.

(Continued)

*Primary Examiner* — Pancham Bakshi
(74) *Attorney, Agent, or Firm* — Seed IP Law Group LLP

(57) ABSTRACT

Provided are methods for isolating biomolecules, such as nucleic acids and proteins, from a sample using a silica-containing surface and/or a high salt, low pH buffer.

46 Claims, 6 Drawing Sheets

(56) References Cited

FOREIGN PATENT DOCUMENTS

| | | |
|---|---|---|
| EP | 2 479 274 A1 | 7/2012 |
| EP | 1 756 136 B1 | 10/2014 |
| WO | 96/18731 A2 | 6/1996 |
| WO | 02/055737 A1 | 7/2002 |
| WO | 03/046146 A2 | 6/2003 |
| WO | 2004/108925 A1 | 12/2004 |
| WO | 2006/073472 A2 | 7/2006 |
| WO | 2006/130720 A2 | 12/2006 |
| WO | 2006/138553 A2 | 12/2006 |
| WO | 2007/140417 A2 | 12/2007 |
| WO | 2008/043551 A1 | 4/2008 |
| WO | 2009/014415 A1 | 1/2009 |
| WO | 2009/025690 A2 | 2/2009 |
| WO | 2009/134652 A1 | 11/2009 |
| WO | 2009/140313 A1 | 11/2009 |
| WO | 2012/135081 A2 | 10/2012 |
| WO | 2014/122288 A1 | 8/2014 |
| WO | 2015/003060 A1 | 1/2015 |
| WO | 2017/041013 A1 | 3/2017 |
| WO | 2017/044827 A1 | 3/2017 |

OTHER PUBLICATIONS

Collins, "Sticky ions in biological systems," *Proc. Natl. Acad. Sci. USA* 92:5553-5557, 1995.

Dijkmans et al., "Rapid method for purification of soil DNA for hybridization and PCR analysis," *Microb Releases* 2:29-34, 1993.

Grasso et al., "Overexpression and Purification of Mammalian Mitochondrial Translational Initiation Factor 2 and Initiation Factor 3," *Methods in Enzymology* 430:59-78, 2007.

Kozlowski, "Proteome-pI: proteome isoelectric point database," *Nucleic Acids Research*:1-5, 2016.

Macfarlane et al., "Isolating RNA From Clinical Samples with Catrimox-14 and Lithium Chloride," *Journal of Clinical Laboratory Analysis* 11:132-139, 1997.

Merriam-Webster, "Definition of anti-foaming," retrieved Jul. 4, 2019 from https://www.merriam-webster.com/dictionary/anti-foaming (2 pages).

MO BIO Laboratories, Inc., "AllPrep® Bacterial DNA/RNA/Protein Kit (50)," Catalog No. 47054, 2016 (24 pages).

MO BIO Laboratories, Inc., "NoviPure™ Soil Protein Extraction Kit," Instruction Manual, Catalog No. 30000-20, 2013 (20 pages).

MO BIO Laboratories, Inc., "PowerFecal® DNA Isolation Kit," Instruction Manual, Catalog No. 12830-50, 2013 (16 pages).

MO BIO Laboratories, Inc., "RNA PowerSoil® Total RNA Isolation Kit," Instruction Manual, Catalog No. 12866-25, 2016 (15 pages).

Qiagen, "AllPrep® DNA/RNA Kits," 2015 (4 pages).

Qiagen, "DNeasy® PowerSoil® Kit Handbook: For the isolation of microbial genomic DNA from all soil types," 2017 (24 pages).

Qiagen, "QIAamp® DNA Stool handbook, For DNA purification from stool samples," Second Edition, Jun. 2012 (44 pages).

Schneegurt et al., "Direct Extraction of DNA from Soils for Studies in Microbial Ecology," *Curr. Issues Mol. Biol.* 5:1-8, 2003.

Shaw et al., "A Simple Procedure for Isolation of DNA, RNA and Protein Fractions from Cultured Animal Cells," *Analytical Biochemistry* 65:125-131, 1975.

Tan et al., "DNA, RNA, and Protein Extraction: The Past and The Present," *Journal of Biomedicine and Biotechnology* 2009(574398):1-10, 2009.

Thatcher, "DNA/RNA Preparation for Molecular Detection," *Clinical Chemistry* 61(1):1-11, 2015.

Triant et al., "Simultaneous Extraction of High-Quality RNA and DNA from Small Tissue Samples," *Journal of Heredity* 100(2):246-250, 2009.

Wikipedia, "Sodium chloride," accessed Sep. 14, 2020 from https://en.wikipedia.org/wiki/Sodium_chloride (9 pages).

Wilkens et al., "Bacteriolysis of *Streptococcus mutans* GS5 by Lysozyme, Proteases, and Sodium Thiocyanate," *Infection and Immunity* 38(3): 1172-1180, 1982.

Willner et al., "Comparison of DNA Extraction Methods for Microbial Community Profiling with an Application to Pediatric Bronchoalveolar Lavage Samples," *PLOS One* 7(4):e34605, 2012 (12 pages).

Yeates et al., "Methods for microbial DNA extraction from soil for PCR amplification," *Biological Procedures Online* 1(1):40-47, 1998.

Zahuczky et al., "Cloning of the bovine leukemia virus proteinase in *Escherichia coli* and comparison of its specificity to that of human T-cell leukemia virus proteinase," *Biochimica et Biophysica Acta* 1478:1-8, 2000.

\* cited by examiner

METHODS FOR CO-ISOLATION OF NUCLEIC ACIDS AND PROTEINS

CROSS-REFERENCE TO RELATED APPLICATIONS

This application is a U.S. National Phase Application of International Application No. PCT/US2016/050197, filed Sep. 2, 2016, which claims priority to and the benefit of U.S. Provisional Application No. 62/214,877, filed Sep. 4, 2015, the contents of which are incorporated by reference herein in their entirety.

FIELD

Provided are methods and compositions, e.g., kits, for isolation of nucleic acids and/or proteins from a sample. In particular embodiments, disclosed herein are methods and compositions for isolation of nucleic acids and proteins on a silica-containing surface.

BACKGROUND

The increased use of DNA, RNA, and proteins in a wide variety molecular biology applications has created a need for fast, simple and reliable methods and reagents for isolating DNA, RNA, and proteins. In many applications, collecting a biological sample and subsequent analysis thereof would be substantially simplified if biomolecules contained within the sample, e.g., DNA, RNA, and proteins, could be co-isolated from a single sample. This co-isolation is especially important when the sample size is small, such as in biopsy, that it precludes its separation into smaller samples to perform separate isolation protocols for DNA, RNA, and proteins.

There are known methods for isolating DNA, RNA, and proteins from biological samples. An important limitation of known methods is that large samples volumes may be needed, e.g., so the sample can be split to perform separate isolations of the biomolecules, e.g., DNA, RNA, and protein. Further disadvantages of known methods include that a prolonged time may be required for isolation, particularly when various biomolecules require separate isolation. Other drawbacks of known methods include the use of toxic solutions, e.g., phenol, low yield of the nucleic acid or protein, a limited number and size of samples that can be processed, and the potential for contamination, such as protein contamination in nucleic acid fractions. High cost of equipment, e.g., ultracentrifuges, can be a further limitation of particular known methods.

The present methods and compositions, e.g., kits, involve a buffer chemistry to bind one or more biomolecules to a silica-containing surface, e.g., glass fiber membranes. The present methods and conditions bring about the binding of both nucleic acids and proteins on a silica-containing surface, e.g., borosilicate glass fibers, silicon dioxide, or silica-coated magnetic beads. Accordingly, provided herein are simple and effective methods and products for the co-isolation of DNA, RNA, and proteins from a single sample for subsequent use in molecular biology, biotechnology, clinical research and other applications.

SUMMARY

In one aspect, provided herein is a method for the isolation of RNA and protein from a sample, the method including a) contacting the sample with a silica-containing surface, whereby the silica-containing surface binds substantially all of the RNA and protein present in the sample; and b) separating the silica-containing surface containing bound RNA and protein from one or more other components of the sample.

In some embodiments, the method further includes following step a): centrifuging the silica-containing surface. In some embodiments, the sample contains substantially no DNA. In some embodiments, substantially no DNA is bound to the silica-containing surface. In some embodiments, step b) further includes binding substantially all DNA comprised in the sample to the silica-containing surface.

In some embodiments, the sample contains a buffer having a pH of less than 4 and a concentration of chloride salt of greater than 2 M. In some embodiments, the chloride salt contains sodium, lithium, potassium, cesium, magnesium, calcium, strontium, zinc, copper, manganese, erbium, holmium, aluminum, or antimony. In some embodiments, the chloride salt contains sodium. In some embodiments, the buffer contains citrate.

In some embodiments, the method further includes eluting the RNA and protein from the silica-containing surface. In some embodiments, the RNA and protein are eluted sequentially. In some embodiments, the RNA is eluted with RNase-free water or TE buffer. In some embodiments, the protein is eluted with a buffer containing Tris with a pH of about 8.0 and 0.5-1% sodium dodecyl sulfate.

In some embodiments, the silica-containing surface contains borosilicate glass fibers or silicon dioxide glass fibers. In some embodiments, the silica-containing surface contains silica-coated magnetic beads. In some embodiments, the one or more other components of the sample are biomolecules.

In another aspect, provided herein is a method for the isolation of DNA, RNA, and protein from a sample, the method including a) contacting the sample with a silica-containing surface; b) binding substantially all of the DNA present in the sample to the silica-containing surface; c) separating the silica-containing surface containing bound DNA from a portion of the sample containing RNA, protein, and one or more other components; d) eluting the DNA from the silica-containing surface; e) contacting the portion of the sample containing RNA, protein, and one or more other components with the silica-containing surface, whereby the silica-containing surface binds substantially all of the RNA and protein present in the portion of the sample containing RNA, protein, and one or more other components; and f) separating the silica-containing surface containing bound RNA and protein from the one or more other components.

In some embodiments, the method further includes following steps a) and e): centrifuging the silica-containing surface. In some embodiments, substantially no RNA or protein is bound to the silica-containing surface in steps a)-d). In some embodiments, in step a) the sample contains a first buffer comprising guanidinium thiocyanate, and wherein the sample is substantially free of organic solvent. In some embodiments, the concentration of guanidinium thiocyanate in the first buffer is greater than 1 M. In some embodiments, in step e) the portion of the sample containing RNA, protein, and one or more other components contains a second buffer having a pH of less than 4 and a concentration of chloride salt of greater than 2 M.

In some embodiments, the chloride salt contains sodium, lithium, potassium, cesium, magnesium, calcium, strontium, zinc, copper, manganese, erbium, holmium, aluminum, or antimony. In some embodiments, the chloride salt contains sodium. In some embodiments, the second buffer contains citrate. In some embodiments, the method further includes following step d): combining the portion of the sample comprising RNA, protein, and one or more other components in the first buffer with the second buffer.

In some embodiments, the method further includes eluting the RNA and protein from the silica-containing surface. In some embodiments, the RNA and protein are eluted sequentially. In some embodiments, the RNA is eluted with RNase-free water or TE buffer. In some embodiments, the protein is eluted with a buffer containing Tris with a pH of about 8.0 and 0.5-1% sodium dodecyl sulfate. In some embodiments, the RNA and DNA are simultaneously eluted from the silica-containing surface. In some embodiments, the DNA is eluted with DNase/RNase-free water, TE buffer, or buffer containing Tris with a pH of about 8.0.

In some embodiments, the silica-containing surface contains borosilicate glass fibers or silicon dioxide glass fibers. In some embodiments, the silica-containing surface contains silica-coated magnetic beads. In some embodiments, the one or more other components in the sample are biomolecules.

In another aspect, provided herein is a method for the isolation of protein from a sample, the method including a) contacting the sample with a silica-containing surface in the presence of a high salt, low pH buffer; and b) separating the silica-containing surface containing bound protein from one or more other components of the sample.

In some embodiments, the method includes following step a), substantially all of the protein present in the sample is bound to the silica-containing surface. In some embodiments, the high salt, low pH buffer has a pH of less than 4 and a concentration of chloride salt of greater than 2 M.

In some embodiments, the chloride salt contains sodium, lithium, potassium, cesium, magnesium, calcium, strontium, zinc, copper, manganese, erbium, holmium, aluminum, or antimony. In some embodiments, the chloride salt contains sodium.

In some embodiments, prior to step a), the sample is contacted with a lysis buffer. In some embodiments, the lysis buffer contains 3M to 6M guanidinium thiocyanate.

In some embodiments, the silica-containing surface contains borosilicate glass fibers or silicon dioxide glass fibers. In some embodiments, the silica-containing surface contains silica-coated magnetic beads. In some embodiments, the one or more other components in the sample are biomolecules.

In another aspect, provided herein is a kit for the isolation of RNA and protein from a sample, containing (a) a silica-containing surface; (b) a buffer having a pH of less than 4 and a concentration of a chloride salt of greater than 4 M; and (c) instructions describing a method for use according to any of the methods described herein.

In another aspect, provided herein is a kit for the isolation of DNA, RNA, and protein from a sample, containing (a) a silica-containing surface; (b) a first buffer comprising guanidinium thiocyanate at a concentration of greater than 5 M; (c) a second buffer having a pH of less than 4 and a concentration of chloride salt of greater than 4 M; and (d) instructions describing a method for use according to any of the methods described herein.

In another aspect, provided herein is a kit for the isolation of protein from a sample, containing (a) a silica-containing surface; (b) a buffer having a pH of less than 4 and a concentration of a chloride salt of greater than 4 M; and (c) instructions describing a method for use according to any of the methods described herein.

DETAILED DESCRIPTION

Figure 1:
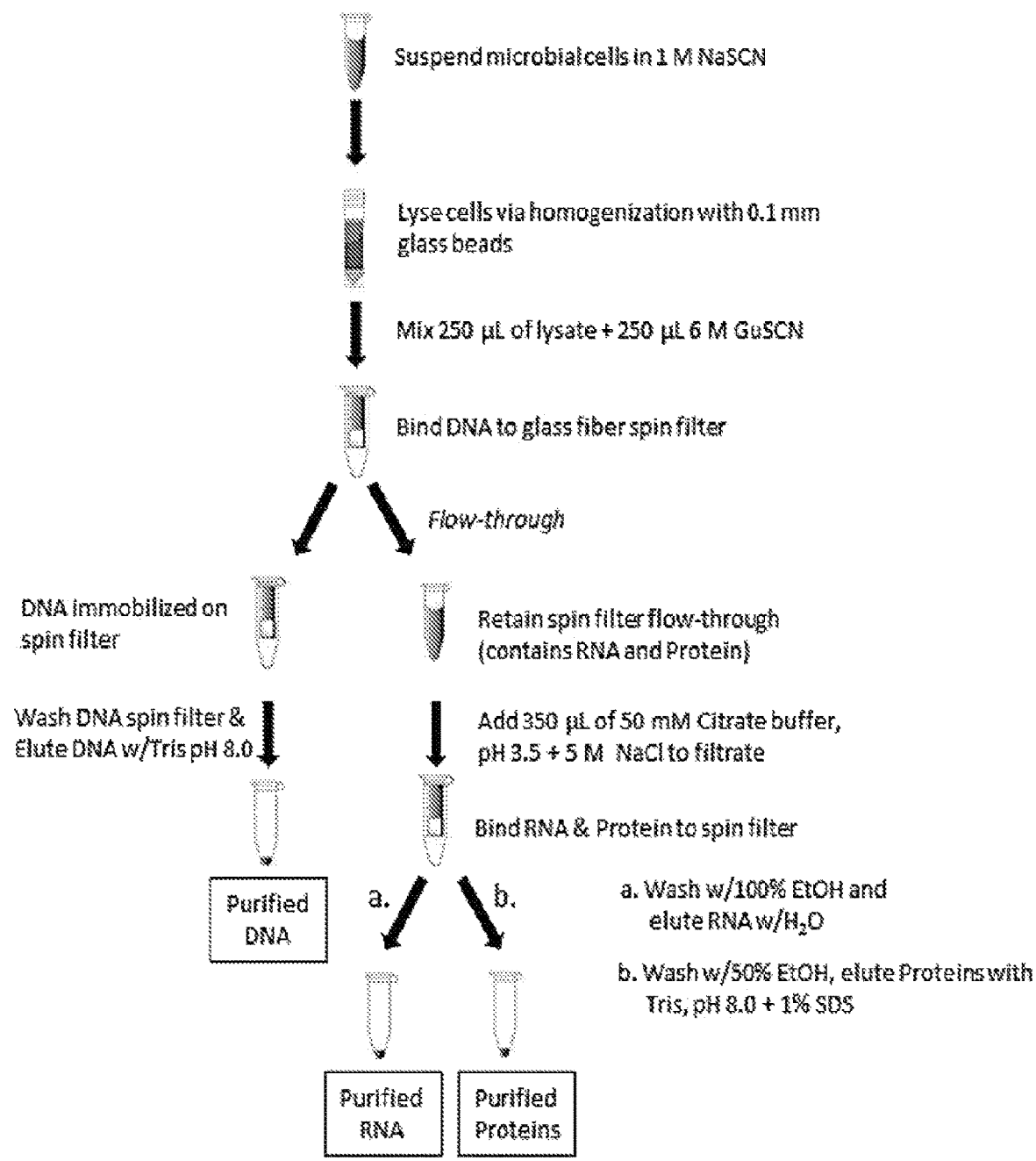
FIG. 1 is a schematic of an exemplary procedure in which DNA is isolated first from a sample, followed by co-isolation of RNA and protein.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y., all of which are herein incorporated in their entireties by reference for all purposes.

I. Methods for Isolation of Nucleic Acids and Proteins on a Silica-Containing Surface Provided are methods and compositions, e.g., kits, for isolation of biomolecules, e.g., proteins and nucleic acids, such as DNA and RNA, from a sample, e.g., a biological sample. In some embodiments, one or more biomolecules are co-isolated with one or more other biomolecules from the same sample. For example, in some aspects, RNA and protein bind to a silica-containing surface in a single step. In other aspects, DNA, RNA, and protein bind to a silica-containing surface in a single step according to the provided methods. In some aspects, the methods include purifying a biomolecule, e.g., protein, DNA, or RNA, from a biological sample such that it is substantially free of other components present in the biological sample.

In some embodiments, the methods include contacting the sample with a silica-containing surface, thereby binding the biomolecule to the surface, and separating the biomolecule from one or more other components of the sample, such as other biomolecules. The contacting, binding, or separating can be carried out sequentially or simultaneously for various biomolecules, e.g., DNA, RNA, and protein. In some instances, conditions are provided such that DNA binds to the silica-containing surface and substantially no RNA or protein is bound. In some instances, conditions are provided such that protein is bound to the silica-containing surface and substantially no RNA or DNA is bound. In other embodiments, conditions are provided such that DNA, RNA, and protein are bound to the silica-containing surface, e.g., simultaneously. In further aspects, conditions are provided such that RNA and protein are bound to the silica-containing surface, e.g., simultaneously, and substantially no DNA is bound. Once bound to the silica-containing surface, the biomolecules may be released, e.g., eluted, from the silica-containing surface simultaneously or sequentially in any order. In some variations or any of the methods described herein, nucleic acids and/or proteins bind to the silica-containing surface in the presence of a high salt, low pH buffer.

Advantages of the present methods can include that multiple biomolecules may be isolated from the same sample. This, in turn, may allow for small sample volumes to be used which can decrease the amount of sample necessary for the isolation and purification of multiple biomolecules.

Samples

The methods provided herein generally involve isolating biomolecules, e.g., nucleic acids and proteins, from other components in a sample, e.g., a biological sample.

As used herein, a "sample" can comprise a naturally occurring component, an artificially derived component, and/or a component artificially synthesized, in part or in whole. In some embodiments, the sample is a biological sample. In some embodiments, the sample comprises one or more biomolecules, which can be from a biological sample or artificially synthesized and/or modified.

The term "biological sample" as used herein, refers to a sample obtained from a biological subject, including samples of biological tissue or fluid origin obtained in vivo or in vitro. Such samples can be, but are not limited to, body fluid (e.g., blood, blood plasma, serum, or urine), organs, tissues, stool, swab samples, and fractions and cells isolated from mammals (e.g., humans). Biological samples also may include sections of the biological sample including tissues (e.g., sectional portions of an organ or tissue). The term "biological sample" may also include extracts from a biological sample, for example, an antigen from a biological fluid (e.g., blood or urine). A biological sample may be of prokaryotic origin (e.g., bacteria, archaea) or eukaryotic origin (e.g., fungi, plants, insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

In some embodiments, the nucleic acids and proteins may be isolated from a single, undivided sample. In this way, the present methods can be distinguished from methods that may involve obtaining multiple samples or dividing a sample into two or more aliquots, from which different biomolecules are isolated. However, subsequent later separation of the initial undivided sample, such as during the contacting and elution steps of the method, is not precluded.

Prior to carrying out nucleic acid and protein isolation procedures, it may be advantageous to lyse any cells in the sample. In such situations it may be desired or convenient to divide the single sample after the cell lysis step has been carried out.

Thus, division of the sample after an initial, or first, binding step, or after two or more binding steps is contemplated. This may be desirable, for example, in order to change conditions (e.g. ionic strength, salt concentration, or pH of buffer), e.g. to isolate different components. Thus, for example, protein and nucleic acid components e.g., DNA and/or RNA, may be isolated from different portions of the sample. Alternatively, in some embodiments, the method is carried out using a single sample which is not divided at any stage or at any time. The fact that the isolation of DNA, RNA, and protein can be carried out on a single, undivided sample using the present methods may be advantageous in that it may allow for a more direct and accurate comparison between the various nucleic acid and protein components of the sample.

Another advantage of the present method is that small sample volumes may be used. For instance, the sample can be 10 µl to 100 ml in size, such as from 200 µl to 10 ml. The sample volume in some aspects is 1 ml or less, e.g. 10 to 800 µl, e.g. 20 to 500 µl, or 50 to 200 µl. Thus, the methods may be used for small samples, e.g., less than 1 ml, or alternatively for larger samples, e.g., at least 2 ml, e.g. more than 5 ml or 10 ml or 50 ml.

In some embodiments, the method may be performed on a sample containing $1\times10^4$ to $1\times10^{10}$ cells, such as $1$-$10\times10^8$ cells. In some aspects, the method described is scalable and can be used to isolate DNA, RNA, and/or protein in 1, 5, 10, 20, 200 or 2000 or more cells.

In some embodiments, the sample contains one or more biomolecules. The term "biomolecules" includes, but is not limited to, nucleic acids and proteins.

The terms "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

An isolated nucleic acid molecule may be one which is separated from other nucleic acid molecules which are present in the sample containing the nucleic acid molecule. An isolated nucleic acid molecule, such as a DNA or RNA molecule, can be substantially free of other cellular material or culture medium, e.g., when produced by recombinant techniques, or substantially free of chemical precursors or other chemicals when chemically synthesized.

Thus, the nucleic acid to be isolated may in some aspects be DNA, RNA, any naturally occurring modification thereof, or combinations thereof. In some aspects, DNA is genomic DNA and may be in a single or double stranded or in any other form.

The term "protein" is used herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

Sample Preparation

In some embodiments, the sample may be contacted with the silica-containing surface under conditions whereby nucleic acids and/or proteins present in the sample will become bound to the silica-containing surface. If necessary, for example, if the nucleic acid and protein to be isolated is not available for binding within the initial sample, such as because it is contained within a biological particle including a viral coat or a cell membrane or wall, the initial binding step may be preceded by one or more separate steps to free the nucleic acid and protein components. Thus, in some aspects, the nucleic acid and protein components are freed by disrupting structural components such as cell walls or membranes to achieve lysis. Procedures for achieving this are known in the art. Although some cells e.g. blood cells, may be lysed by reagents such as detergent alone, other cells, e.g. plant or fungal cells or solid animal tissues may require more vigorous treatment such as, for example, grinding in liquid nitrogen, heating in the presence of detergent, or alkaline lysis in the presence of detergent. In some embodiments, procedures for freeing the nucleic acid and protein are chosen such that the particular nucleic acid and protein species which are to be isolated by the methods described herein remain sufficiently intact, e.g., are not substantially degraded.

In some embodiments, for example in cases where the nucleic acid and protein to be isolated is contained within a cell, the cell is first processed by lysing or disrupting the cell to produce a lysate. In some aspects, the cell is additionally processed by clearing the lysate of cellular debris (e.g., by centrifugation or vacuum filtration), such as debris that may interfere with adhesion of the nucleic acid or protein to the silica-containing surface.

Lysing may refer to any process in which the integrity of the cellular membrane of a cell is compromised to the point that at least some of the cellular contents, including but not limited to DNA, RNA, and protein, are released. Any number of well-known chemical or physical cell lysis techniques can be used in the present methods. For example, in some embodiments, a lysis solution comprising one or more detergents is employed to lyse the cells, including without limitation, solutions comprising nonionic detergents, anionic detergents, cationic detergents, zwitterionic detergents, or combinations thereof. In some embodiments, solutions comprising chaotropes are employed to lyse cells, including but not limited to solutions comprising guanidinium thiocyanate, guanidine hydrochloride, potassium thiocyanate, or urea, and combinations thereof. In some aspects, a solution comprising at least one detergent and at least one chaotrope is used to lyse the cells. In some embodiments, cells are lysed by physical forces such as shear forces, osmotic shock, or sonication using methods and apparatuses known in the art.

Thus, any one of a number of different methods for lysing or disrupting cells to release nucleic acids and proteins contained therein is suitable. In some embodiments, the method chosen to release the nucleic acid and protein from a cell will depend upon the nature of the cell containing the material. For instance, in order to cause a cell with a relatively hard cell wall, such as a fungus cell or a plant cell, to release the nucleic acid material contained therein one may need to use harsh treatments such as potent proteases and mechanical shearing with a homogenizer or disruption with sound waves using a sonicator. In other aspects, nucleic acid material can be readily released from cells with lipid bi-layer membranes such as bacteria or animal blood cells by suspending such cells in an aqueous solution and adding a detergent to the solution.

In some embodiments, cells are lysed via homogenization, such as with beads. The beads may be made of any solid material that is non-reactive with the samples, solutions, or other reagents used in the method. The beads may be round or irregularly shaped. The beads may be of uniform size or of varying sizes. The beads may be of uniform material or of heterogeneous material. In some variations, the beads are ceramic. In some variations, the beads are glass. In some variations, the beads have an average diameter of 0.01 to 10, 0.1 to 5, 0.1 to 3, 0.2 to 3, 0.1 to 2, or 1 to 3 mm. In some variation the beads have an average diameter of at least about 0.01, about 0.1, about 0.2, about 0.5, about 1, about 2, about 3, or about 5 mm. In some variations, the beads have an average diameter of up to about 0.1, about 0.2, about 0.5, about 1, about 2, about 3, about 5, or about 10 mm. In some instances, the beads are 0.2, 1.4, or 2.8 mm ceramic beads. In some instances, the beads are 0.1 or 0.5 mm glass beads. In a particular variation, the beads are 0.2 mm ceramic beads. In another particular variation, the beads are 0.1 mm glass beads. In yet another particular variation, the beads are a mixture of 0.1 mm glass beads and 0.2 mm ceramic beads. Agitation of the sample in the presence of beads may be achieved by physical force, such as shaking or vibration. Vibration can be introduced by any convenient means, such as by a sonication or a vortex apparatus using a Vortex Adapter (Mo Bio Laboratories, Carlsbad, Calif.), for example.

In some variations, the cells are lysed under conditions that allow for protein and nucleic acids to be released (e.g., 1M NaSCN). In other variations, the cells are lysed under conditions that allow for protein to be released, but wherein the nucleic acids may be degraded as a consequence of the strength of the chaotropic agent when combined with mechanical homogenization (e.g., 1M to 6M guanidinium thiocyanate).

Silica-Containing Surface

As described herein, the sample is contacted with a silica-containing surface.

Certain aspects of the present disclosure relate to the use of silica-containing surfaces, e.g., to bind and separate RNA and protein from DNA and other materials, or to bind and elute DNA from RNA and protein. In some embodiments, the silica-containing surface comprises a porous membrane or filter, such as a silica-based material, including but not limited to a glass fiber filter or a glass frit. In some embodiments, the capture surface is non-porous, such as certain planar surfaces or non-planar surfaces, including without limitation, beads or particles, for example but not limited to, glass beads and coated magnetic or paramagnetic beads.

In some embodiments, a silica-containing surface of the present disclosure comprises a borosilicate (e.g., a borosilicate glass). In some embodiments, a silica-containing surface of the present disclosure comprises silicon dioxide. A variety of silica-containing materials are known in the art, including, without limitation, silica glasses (e.g., glass particles, common silicate glass, powder, and microfibers), diatomaceous earth or diatomite, flint glass, zeolite and other aluminosilicate minerals, hydrated silica compounds (e.g., as described in U.S. Pat. No. 5,342,931), and the like.

In some embodiments, a silica-containing surface of the present disclosure comprises a glass fiber (e.g., a borosilicate or silicon dioxide glass fiber). In some embodiments, a silica-containing surface of the present disclosure comprises a silica-coated magnetic bead. In some embodiments, a silica-containing surface of the present disclosure is used as part of a filter suitable for centrifugation or other solid phase extraction, such as a spin filter or spin column. In some embodiments, a silica-containing surface of the present disclosure is used as part of a component suitable for solid phase extraction from other materials (e.g., a lysate or flow-through), such as a bead that may be centrifuged and/or magnetically separated from other materials.

Buffers

In some embodiments, the sample contains or is combined with one or more buffers.

The buffer may be a basic buffer. The buffer may be any buffer that is amenable to culturing cells. The buffer may be any buffer that is useful for maintaining the sample at physiological pH. The buffer used in the compositions and methods described herein may include or may contain, one of more of the following: Tris Base (tris(hydroxymethyl) aminomethane), Bis-Tris (Bis(2-hydroxyethyl)-amino-tris (hydroxymethyl)-methane), HEPES (4-(2-hydroxyethyl)-1-piperazineethanesulfonic acid), PBS (phosphate buffered saline), MOPS (3-(N-morpholino)propanesulfonic acid), MES (2-(N-morpholino)ethanesulfonic acid), and CAPS (N-cyclohexyl-3-aminopropanesulfonic acid).

In some embodiments, the sample contains or is mixed with a high salt, low pH buffer. In particular, the sample may contact the silica-containing surface in the presence of a high salt, low pH buffer. In some embodiments, the high salt, low pH buffer has a pH of less than or equal to 4.0 and a salt (e.g., NaCl) concentration greater than 4 M. It is a surprising result of the present disclosure that both RNA and protein may be simultaneously co-isolated from other cellular materials (e.g., DNA, lipids, etc.) on a substrate (including but not limited to a borosilicate glass or silicon dioxide substrate) by combining a crude sample that contains RNA and protein (e.g., a cell lysate) with a buffer having a pH of less than or equal to 4.0 and a concentration of chloride salt of greater than 4 M in the presence of the substrate. The buffer may be any buffer that is useful for maintaining the sample at the desired pH (e.g., less than or equal to 4.0). In some embodiments, suitable buffers may include, without limitation, acidic buffers such as citrate, sodium acetate, glycine-HCl, and phosphate-citrate buffers. In certain embodiments, the buffer comprises citrate. In certain embodiments, the buffering system is capable of providing and maintaining a pH in the range of 2-4 (e.g., 3.5). In some embodiments, the concentration of NaCl or other salt is diluted upon mixing with the sample to provide a final NaCl or other salt concentration of greater than about 2.0 M.

In some embodiments, the buffer having a pH of less than or equal to 4.0 has a salt concentration of greater than 1M, greater than 2M, greater than 3M, or greater than 4M. For example, in some embodiments, the buffer has a pH of less than or equal to 4.0 and a salt concentration of greater than about 4.0M, greater than about 4.1M, greater than about 4.2M, greater than about 4.3M, greater than about 4.4M, greater than about 4.5M, greater than about 4.6M, greater than about 4.7M, greater than about 4.8M, greater than about 4.9M, greater than about 5.0M, greater than about 5.1M, greater than about 5.2M, greater than about 5.3M, greater than about 5.4M, greater than about 5.5M, greater than about 5.6M, greater than about 5.7M, greater than about 5.8M, greater than about 5.9M, or greater than about 6.0M. In some embodiments, the upper limit of salt concentration may depend upon the upper limit of water solubility of the particular salt under desired temperature and pressure conditions. For example, in some embodiments (e.g., a NaCl salt), the buffer has a pH of less than or equal to 4.0 and a salt concentration of greater than about 1.0M, greater than about 2.0M, greater than about 3.0M, greater than about 4.0M, greater than about 4.1M, greater than about 4.2M, greater than about 4.3M, greater than about 4.4M, greater than about 4.5M, greater than about 4.6M, greater than about 4.7M, greater than about 4.8M, greater than about 4.9M, greater than about 5.0M, greater than about 5.1M, greater than about 5.2M, greater than about 5.3M, greater than about 5.4M, greater than about 5.5M, greater than about 5.6M, greater than about 5.7M, greater than about 5.8M, greater than about 5.9M, or greater than about 6.0M, and the salt concentration is less than or equal to about 6.5M.

Various salts known in the art may be used in the buffer having a pH of less than or equal to 4.0 and a salt concentration greater than 4 M. In some embodiments, the salt is a monobasic salt. In some embodiments, the salt is an alkali metal salt, e.g., a lithium, sodium, potassium, cesium, or rubidium salt. In other embodiments, the salt is a dibasic salt. In some embodiments, the salt is an alkaline earth metal salt, e.g., a magnesium, calcium, or strontium salt. In some embodiments, the salt is a transition element, lanthanide, or other metal salt, e.g., a zinc, copper, manganese, erbium, holmium, aluminum, or antimony salt. In some embodiments, the salt comprises sodium and/or chloride. In some embodiments, the salt comprises fluoride, bromide, or iodide. In certain embodiments, the salt is sodium chloride (NaCl).

In some embodiments, the buffer having a salt concentration of greater than 1M (e.g., greater than 2M, greater than 3M, or greater than 4M) has a pH of less than or equal to 4.0. For example, in some embodiments, the buffer has a salt concentration of greater than 1M (e.g., greater than 2M, greater than 3M, or greater than 4M) and a pH of less than or equal to about 4.0, less than or equal to about 3.9, less than or equal to about 3.8, less than or equal to about 3.7, less than or equal to about 3.6, less than or equal to about 3.5, less than or equal to about 3.4, less than or equal to about 3.3, less than or equal to about 3.6, less than or equal to about 3.5, less than or equal to about 3.4, less than or equal to about 3.3, less than or equal to about 3.2, less than or equal to about 3.1, less than or equal to about 3.0, less than or equal to about 2.9, less than or equal to about 2.8, less than or equal to about 2.7, less than or equal to about 2.6, or less than or equal to about 2.5. In some embodiments, the lower limit of pH may depend upon the particular buffer. For example, in some embodiments (e.g., a citrate buffer), the buffer has a salt concentration of greater than 4M and a pH of less than or equal to about 4.0, less than or equal to about 3.9, less than or equal to about 3.8, less than or equal to about 3.7, less than or equal to about 3.6, less than or equal to about 3.5, less than or equal to about 3.4, less than or equal to about 3.3, less than or equal to about 3.6, less than or equal to about 3.5, less than or equal to about 3.4, less than or equal to about 3.3, less than or equal to about 3.2, or less than or equal to about 3.1, and the pH is greater than or equal to about 3.0.

In some embodiments, the buffer has a salt concentration of greater than about 1.0M, greater than about 2.0M, greater than about 3.0M, greater than about 3.2M, greater than about 3.5M, greater than about 4.0M, greater than about 4.1M, greater than about 4.2M, greater than about 4.3M, greater than about 4.4M, greater than about 4.5M, greater than about 4.6M, greater than about 4.7M, greater than about 4.8M, greater than about 4.9M, greater than about 5.0M, greater than about 5.1M, greater than about 5.2M, greater than about 5.3M, greater than about 5.4M, greater than about 5.5M, greater than about 5.6M, greater than about 5.7M, greater than about 5.8M, greater than about 5.9M, or greater than about 6.0M and has a pH of less than or equal to about 4.0, less than or equal to about 3.9, less than or equal to about 3.8, less than or equal to about 3.7, less than or equal to about 3.6, less than or equal to about 3.5, less than or equal to about 3.4, less than or equal to about 3.3, less than or equal to about 3.6, less than or equal to about 3.5, less than or equal to about 3.4, less than or equal to about 3.3, less than or equal to about 3.2, less than or equal to about 3.1, less than or equal to about 3.0, less than or equal to about 2.9, less than or equal to about 2.8, less than or equal to about 2.7, less than or equal to about 2.6, or less than or equal to about 2.5. In some embodiments, the buffer has a salt concentration of greater than about 1.0M, greater than about 2.0M, greater than about 3.0M, greater than about 4.0M, greater than about 4.1M, greater than about 4.2M, greater than about 4.3M, greater than about 4.4M, greater than about 4.5M, greater than about 4.6M, greater than about 4.7M, greater than about 4.8M, greater than about 4.9M, greater than about 5.0M, greater than about 5.1M, greater than about 5.2M, greater than about 5.3M, greater than about 5.4M, greater than about 5.5M, greater than about 5.6M, greater than about 5.7M, greater than about 5.8M, greater than about 5.9M, or greater than about 6.0M, but less than or equal to about 6.5M, and has a pH of less than or equal to about 4.0, less than or equal to about 3.9, less than or equal to about 3.8, less than or equal to about 3.7, less than or equal to about 3.6, less than or equal to about 3.5, less than or equal to about 3.4, less than or equal to about 3.3, less than or equal to about 3.6, less than or equal to about 3.5, less than or equal to about 3.4, less than or equal to about 3.3, less than or equal to about 3.2, or less than or equal to about 3.1, but greater than or equal to about 3.0.

In some embodiments, the buffer having a salt concentration of greater than 3M (e.g., greater than 4M) and a pH of less than or equal to 4.0 may be present in a buffer concentration of from about 1 to 200, 10 to 100, 10 to 80, 1 to 50, 1 to 20, 10 to 50, 10 to 30, 10 to 20, 20 to 50, or 15 to 25 mM. The concentration of the buffer, in some aspects, is greater than about 1, about 10, about 20, about 30, about 40, about 50, about 60, about 70, about 80, about 90, or about 100 mM buffer. The concentration of the buffer, in some aspects, is less than about 10, about 20, about 30, about 40, about 50, about 60, about 70, about 80, about 90, about 100, about 150, or about 200 mM buffer. One of skill in the art may suitably select a buffer concentration, which in some cases may depend upon the biomolecule(s) of interest, the separation method(s), and/or the type of buffer.

It is to be understood that some or all of the pH levels and/or salt concentrations described above may be combined with some or all of the buffers, buffer concentrations and/or salts described above. One of skill in the art may select a salt concentration and pH suitable for any of the buffers and/or salts described herein. For example, in some embodiments, the buffer is a citrate buffer having a NaCl concentration of greater than about 1.0M, greater than about 2.0M, greater than about 3.0M, greater than about 3.2M, greater than about 3.5M, greater than about 4.0M, greater than about 4.1M, greater than about 4.2M, greater than about 4.3M, greater than about 4.4M, greater than about 4.5M, greater than about 4.6M, greater than about 4.7M, greater than about 4.8M, greater than about 4.9M, greater than about 5.0M, greater than about 5.1M, greater than about 5.2M, greater than about 5.3M, greater than about 5.4M, greater than about 5.5M, greater than about 5.6M, greater than about 5.7M, greater than about 5.8M, greater than about 5.9M, or greater than about 6.0M, but less than or equal to about 6.5M, and a pH of less than or equal to about 4.0, less than or equal to about 3.9, less than or equal to about 3.8, less than or equal to about 3.7, less than or equal to about 3.6, less than or equal to about 3.5, less than or equal to about 3.4, less than or equal to about 3.3, less than or equal to about 3.6, less than or equal to about 3.5, less than or equal to about 3.4, less than or equal to about 3.3, less than or equal to about 3.2, or less than or equal to about 3.1, but greater than or equal to about 3.0. In certain embodiments, the buffer is a 50 mM citrate buffer, pH 3.5, with 5M NaCl.

Other aspects of the present disclosure relate to buffers comprising a guanidinium salt, e.g., guanidinium thiocyanate (GuSCN) or guanidinium hydrochloride (GuHCl). In some variations, such buffers may be used to achieve DNA binding. Alternative chaotropic agents for achieving DNA binding are known in the art (e.g., NaI, NaClO$_4$, NaSCN) and may, in some embodiments, be substituted for or used in combination with a guanidinium salt. In some embodiments, the buffer comprising the guanidinium salt (e.g., GuSCN) is substantially free of organic solvent. For example, in some embodiments, the buffer is, at least about 90%, at least about 91%, at least about 92%, at least about 93%, at least about 94%, at least about 95%, at least about 96%, at least about 97%, at least about 98%, or at least about 99% free of organic solvent. In some embodiments, the buffer comprises a high molarity of the guanidinium salt (e.g., GuSCN). For example, in some embodiments, the buffer comprises greater than about 5M guanidinium salt (e.g., GuSCN), greater than about 5.5M guanidinium salt (e.g., GuSCN), greater than about 6M guanidinium salt (e.g., GuSCN), greater than about 6.5M guanidinium salt (e.g., GuSCN), greater than about 7M guanidinium salt (e.g., GuSCN), or greater than about 7.5M guanidinium salt (e.g., GuSCN). In some embodiments, the buffer comprises greater than about 5M guanidinium salt (e.g., GuSCN), greater than about 5.5M guanidinium salt (e.g., GuSCN), greater than about 6M guanidinium salt (e.g., GuSCN), greater than about 6.5M guanidinium salt (e.g., GuSCN), greater than about 7M guanidinium salt (e.g., GuSCN), or greater than about 7.5M guanidinium salt (e.g., GuSCN), but less than or equal to about 8M guanidinium salt (e.g., GuSCN).

Binding of Biomolecules to Silica-Containing Surface

In some embodiments, biomolecules contained in the sample, e.g., DNA, RNA, and protein, can bind to the silica-containing surface.

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds.

As used herein in reference to binding, "substantially all" of one or more substances (e.g., RNA and protein) from a sample are considered bound to a substrate (e.g., a silica-containing surface) when the amount of the one or more substances still present in the sample after contact and subsequent separation of the sample from the substrate is considered negligible. In some embodiments, "substantially all" of one or more substances (e.g., RNA and protein) from a sample are bound to a substrate (e.g., a silica-containing surface) when greater than about 70 wt. %, greater than about 75 wt. %, greater than about 80 wt. %, greater than about 85 wt. %, greater than about 90 wt. %, greater than about 91 wt. %, greater than about 92 wt. %, greater than about 93 wt. %, greater than about 94 wt. %, greater than about 95 wt. %, greater than about 96 wt. %, greater than about 97 wt. %, greater than about 98 wt. %, greater than about 99 wt. %, or about 100 wt. % of the amount of the one or more substances present in the sample before contact with the substrate remain bound to the substrate after contact with, and subsequent separation from, the sample.

As used herein in reference to binding, one or more substances (e.g., DNA) from a sample are considered to demonstrate "substantially no" binding to a substrate (e.g., a silica-containing surface) when the amount of the one or more substances remaining bound to the substrate after separation of the substrate from the sample is considered negligible. In some embodiments, "substantially no" binding of one or more substances (e.g., RNA and protein) from a sample to a substrate (e.g., a silica-containing surface) refers to a condition in which less than about 30 wt. %, less than about 25 wt. %, less than about 20 wt. %, less than about 15 wt. %, less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt. %, or about 0 wt. % of the amount of the one or more substances present in the sample before contact with the substrate remain bound to the substrate after contact with, and subsequent separation from, the sample.

In some embodiments, the sample, e.g., biological sample, is contacted with the silica-containing surface. As described herein, the sample can contain biomolecules, such as DNA, RNA, and proteins, that in some aspects are released from cells contained in the sample, e.g., as described above, e.g., by lysing, prior to the contacting of the sample with the silica-containing surface. For instance, prior to contacting the sample with the silica-containing surface, cells contained in the sample can be suspended in a lysis buffer. The lysis buffer may be any suitable buffer, such as those described above. For example, the lysis buffer may contain NaSCN (e.g., about 1 M NaSCN). In another example, the lysis buffer may contain guanidinium thiocyanate (e.g., about 3M to about 6M guanidinium thiocyanate). In some embodiments, following suspension of the cells in the lysis buffer, the cells are lysed, e.g., as described above, e.g., via homogenization with glass beads, to prepare a cell lysate contained within the sample. In some embodiments, the Thus, in some aspects, when the sample is contacted with the silica-containing surface, biomolecules contained in the sample, e.g., DNA, RNA, and protein, can bind to the silica-containing surface, thereby isolating the biomolecules from the sample, e.g., one or more other components contained in the sample.

i. Binding of RNA and Protein to Silica-Containing Surface

In some aspects, the sample containing RNA and protein and one or more other components contains substantially no DNA. For example, the sample may contain less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % DNA. In some variations, the DNA has been removed from the sample by contacting the sample with a silica-containing surface in the presence of a guanidinium-containing buffer as described herein. In some embodiments, the sample containing RNA and protein and one or more other components is in a solution containing the lysis buffer. In some aspects, the sample is combined with a second buffer, e.g., as described above, such as a high salt, low pH buffer, e.g., containing 50 mM citrate (pH 3.5) and 5 M NaCl.

In some embodiments, the sample containing RNA and protein is contacted with a silica-containing surface. In some variations, the sample containing RNA and protein is contacted with a silica-containing surface in the presence of a high salt, low pH buffer. Such a contacting step may take place under conditions in which the RNA and protein are selectively bound to the silica-containing surface, e.g., glass spin filter or magnetic beads. The RNA and protein, in some aspects, may be bound to the silica-containing surface under the same conditions and/or may be bound simultaneously or substantially simultaneously. In some instances, the silica-containing surface including the sample containing RNA and protein is centrifuged. In some aspects, following the contacting step, substantially all of the RNA and protein are bound to the silica-containing surface. For example, in some aspects at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the RNA and protein in the sample is bound to the silica-containing surface.

An optional wash step can be performed to remove biomolecules or other components of the sample that may have bound nonspecifically to the silica-containing surface during the contacting step. In some embodiments, the silica-containing surface is washed with 100% ethanol, e.g., to remove residual salts.

In some instances, the RNA and protein are released sequentially from the silica-containing surface. RNA may be released, e.g., eluted, from the silica-containing surface with water, e.g., RNase-free water, or TE buffer.

In some embodiments, following elution of the RNA, the silica-containing surface is washed, e.g., with 50% ethanol. Following the optional wash step, the silica-containing surface may be substantially free of RNA. For instance, less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % of the RNA from the sample may remain bound to the silica-containing surface. Thus, in some instances, at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the RNA present in the sample has been purified.

Following the elution of the RNA from the silica-containing surface, proteins can be released, e.g., eluted, from the silica-containing surface, e.g., glass fiber membrane, spin filter, or magnetic beads. In some aspects, a small volume of elution buffer may be used to elute the proteins, for example, less than 10 μL, less than 20 μL, less than 50 μL, less than 100 μL, less than 500 μL, less than 1 mL or less than 5 mL. The buffer used for elution of the proteins may contain Tris, such as Tris having a pH of between or between about 6.0 and 10.0, e.g., between or between about 7.0 and 9.0, or has a pH that is or is about 8.0. In some aspects, the protein elution buffer can contain sodium dodecyl sulfate (SDS), such as 0.01-10.0%, e.g., 0.1-5.0%, or 0.5-1.0% SDS.

In some embodiments, the order of eluting the RNA and protein may be reversed. For example, the protein may be eluted first, followed by an optional wash step and the elution of the RNA from the silica-containing surface.

ii. Binding of DNA, RNA, and Protein to Silica-Containing Surface (Co-Isolation)

In some aspects, a sample containing DNA, RNA, and protein is mixed with a co-isolation buffer, prepared, e.g., as described above. Thus, in some aspects, the co-isolation buffer may contain a mixture of a first buffer, e.g., containing guanidinium thiocyanate (GuSCN), such as at a concentration of 6 M, and a second buffer, e.g., a high salt, low pH buffer such as a buffer containing 50 mM citrate (pH 3.5) and 5 M NaCl.

The sample may be mixed with a volume of the co-isolation buffer that is equal to or is approximately equal to the volume the sample, or may be mixed with a volume of the first buffer that is or is about 0.1 times, 0.5 times, 1.5 times, 2 times, 2.5 times, 3 times, 5 times, 10 times, or more than 10 times the volume of the sample.

In some embodiments, the sample containing the co-isolation buffer is contacted with a silica containing surface. For example, the sample can be passed through a borosilicate glass fiber spin filter, or contacted with silicon dioxide glass fibers, silica-coated magnetic particles, or any other suitable silica-containing surface, such as those described above. In some embodiments, the contacting step includes centrifugation of the silica-containing surface containing the sample. In some embodiments, the contacting step is carried out in the absence of an organic solvent, e.g., ethanol.

Thus, in some aspects, the contacting of the sample with the silica-containing surface results in the binding of DNA, RNA, and protein to the silica-containing surface, e.g., glass fiber membrane or filter. In some embodiments, the various biomolecules are bound to the silica-containing surface simultaneously or substantially simultaneously. Substantially all of the DNA, RNA, and/or protein may be bound to the silica-containing surface. For instance, at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the DNA, RNA, and protein in the sample can be bound to the silica-containing surface.

Following the contacting step, an optional wash step can be performed to remove biomolecules or other components of the sample that may have bound nonspecifically to the silica-containing surface during the contacting step. In some embodiments, the silica-containing surface is washed with 100% ethanol, e.g., to remove residual salts.

Following the optional wash step, the biomolecules can be eluted simultaneously or sequentially. In some instances, the DNA and RNA are eluted simultaneously and protein is released sequentially from the silica-containing surface. DNA and RNA may be released, e.g., eluted, from the silica-containing surface with water, e.g., RNase-free water, or TE buffer.

In some embodiments, following elution of the DNA and RNA, the silica-containing surface is washed, e.g., with 50% ethanol. Thus, following the elution of the DNA and RNA, the silica-containing surface may be substantially free of DNA and RNA. For instance, less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % of the DNA and RNA from the sample may remain bound to the silica-containing surface. Thus, in some instances, at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the DNA and RNA present in the sample has been separated from protein and other components of the sample.

Following the elution of the DNA/RNA from the silica-containing surface, proteins can be released, e.g., eluted, from the silica-containing surface, e.g., glass fiber membrane, spin filter, or magnetic beads. In some aspects, a small volume of elution buffer may be used to elute the proteins, for example, less than 10 μL, less than 20 μL, less than 50 μL, less than 100 μL, less than 500 μL, less than 1 mL or less than 5 mL. The buffer used for elution of the proteins may contain Tris buffer, such as having a pH of between or between about 6.0 and 10.0, e.g., between or between about 7.0 and 9.0, or is or is about pH 8.0. In some aspects, the protein elution buffer can contain sodium dodecyl sulfate (SDS), such as 0.01-10.0%, e.g., 0.1-5.0%, or 0.5-1.0% SDS.

In some embodiments, the order of eluting the DNA/RNA and protein may be reversed. For example, the protein may be eluted first, followed by an optional wash step and the elution of the DNA/RNA from the silica-containing surface.

iii. Binding of DNA, RNA, and Protein to Silica-Containing Surface (Sequential Isolation)

In some aspects, a sample containing DNA, RNA, and protein is mixed with a first buffer. In some embodiments, the first buffer is prepared, e.g., as described above. Thus, in some aspects, the first buffer may contain guanidinium thiocyanate (GuSCN), such as at a concentration of 6 M.

The sample may be mixed with a volume of the first buffer that is equal to or is approximately equal to the volume of the sample, or may be mixed with a volume of the first buffer that is or is about 0.1 times, 0.5 times, 1.5 times, 2 times, 2.5 times, 3 times, 5 times, 10 times, or more than 10 times the volume of the sample.

In some embodiments, the sample containing the first buffer is contacted with a silica containing surface. For example, the sample can be passed through a borosilicate glass fiber spin filter, silicon dioxide glass fibers, silica-coated magnetic particles, or any other silica-containing surface, such as those described above. In some embodiments, the contacting step includes centrifugation of the silica-containing surface containing the sample. In some embodiments, the contacting step is carried out in the absence of an organic solvent, e.g., ethanol.

Thus, in some aspects, the contacting of the sample with the silica-containing surface results in the binding of DNA to the silica-containing surface, e.g., glass fiber membrane or filter. The remainder of the sample, including other biomolecules such as RNA and protein, in some aspects are not bound to the silica-containing surface under these conditions. For example, RNA and protein in the sample may pass through the silica-containing surface, such as membrane or filter. Thus, following the binding of the DNA to the silica-containing surface, the silica-containing surface containing the DNA is separated from the remainder of the sample that contains RNA and protein, which may, for example, be contained in flow-through, that may be saved for a later step.

In some embodiments, the silica-containing surface, e.g., spin filter, is washed to remove any biomolecules or other components of the sample that may have non-specifically bound to the silica-containing surface. In some aspects, following the optional wash step, the DNA is eluted from the silica-containing surface, such as with a buffer containing water, e.g., RNase-free water, TE buffer, or a buffer containing Tris, e.g., Tris with a pH of between or between about 6 and 10, such as between or between about 7 and 9, such as 8.0 or about 8.0.

In some aspects, the portion of the sample containing RNA and protein and one or more other components, e.g. flow-through from DNA-binding step, contains substantially no DNA. For example, the sample may contain less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % DNA. In some embodiments, the portion of the sample containing RNA and protein and one or more other components is in a solution containing a mixture of the lysis buffer and the first buffer. For example, the RNA- and protein-containing portion of the sample may be in a background of 0.5 M NaSCN/3 M GuSCN buffer. In some aspects, this portion of the sample is combined with a second buffer, e.g., as described above, such as a high salt, low pH buffer, e.g., containing 50 mM citrate (pH 3.5) and 5 M NaCl.

In some embodiments, the portion of the sample containing RNA, protein, and one or more other components is contacted with the same or a second silica-containing surface. Such a contacting step may take place under conditions in which the RNA and protein are selectively bound to the silica-containing surface, e.g., glass spin filter or magnetic beads. In some instances, the silica-containing surface including the portion of the sample containing RNA and protein is centrifuged. In some aspects, following the contacting step, substantially all of the RNA and protein are bound to the silica-containing surface. For example, in some aspects at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the RNA and protein in the sample is bound to the silica-containing surface.

An optional wash step can be performed to remove biomolecules or other components of the sample that may have bound nonspecifically to the silica-containing surface during the contacting step. In some embodiments, the silica-containing surface is washed with 100% ethanol, e.g., to remove residual salts.

In some instances, the RNA and protein are released sequentially from the silica-containing surface. RNA may be released, e.g., eluted, from the silica-containing surface with water, e.g., RNase-free water, or TE buffer.

In some embodiments, following elution of the RNA, the silica-containing surface is washed, e.g., with 50% ethanol. Following the optional wash step, the silica-containing surface may be substantially free of RNA. For instance, less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % of the RNA from the sample may remain bound to the silica-containing surface. Thus, in some instances, at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the RNA present in the sample has been purified.

Following the elution of the RNA from the silica-containing surface, proteins can be released, e.g., eluted, from the silica-containing surface, e.g., glass fiber membrane, spin filter, or magnetic beads. In some aspects, a small volume of elution buffer may be used to elute the proteins, for example, less than 10 µL, less than 20 µL, less than 50 µL, less than 100 µL, less than 500 µL, less than 1 mL or less than 5 mL. The buffer used for elution of the proteins may contain Tris buffer, such as having a pH of between or between about 6.0 and 10.0, e.g., between or between about 7.0 and 9.0, or is or is about pH 8.0. In some aspects, the protein elution buffer can contain sodium dodecyl sulfate (SDS), such as 0.01-10.0%, e.g., 0.1-5.0%, or 0.5-1.0% SDS.

In some embodiments, the order of eluting the RNA and protein may be reversed. For example, the protein may be eluted first, followed by an optional wash step and the elution of the RNA from the silica-containing surface.

In some instances, the purity of the resulting protein or nucleic acid is at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. %. In some instances, at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the biomolecule, e.g., nucleic acid or protein, present in the sample is isolated using any of the methods or compositions described herein.

iv. Binding of Protein to Silica-Containing Surface

In some aspects, a sample containing protein and one or more other components contains substantially no nucleic acids. For example, the sample may contain less than 40 wt. %, less than 30 wt. %, less than 20 wt. %, less than 10 wt. %, less than 5 wt. %, less than 2 wt. %, less than 1 wt. %, less than 0.1 wt. %, less than 0.01 wt. %, less than 0.001 wt. %, or less than 0.0001 wt. % nucleic acids. In some variations, the nucleic acids have been removed from the sample during a previous lysis procedure, e.g., as described herein. In some embodiments, the sample containing protein and one or more other components is in a solution containing the lysis buffer. In some aspects, the sample is combined with a second buffer, e.g., as described above, such as a high salt, low pH buffer, e.g., containing 50 mM citrate (pH 3.5) and 5 M NaCl.

In some embodiments, the sample containing protein is contacted with a silica-containing surface. In some variations, the sample containing protein is contacted with a silica-containing surface in the presence of a high salt, low pH buffer. Such a contacting step may take place under conditions in which the substantially all of the protein is bound to the silica-containing surface, e.g., glass spin filter or magnetic beads. In some instances, the silica-containing surface including the sample containing protein is centrifuged. In some aspects, following the contacting step, substantially all of the protein is bound to the silica-containing surface. For example, in some aspects at least 50 wt. %, at least 60 wt. %, at least 70 wt. %, at least 80 wt. %, at least 90 wt. %, at least 95 wt. %, at least 98 wt. %, at least 99 wt. %, at least 99.9 wt. %, or at least 99.99 wt. % of the protein in the sample is bound to the silica-containing surface.

An optional wash step can be performed to remove biomolecules or other components of the sample that may have bound nonspecifically to the silica-containing surface during the contacting step. In some embodiments, the silica-containing surface is washed with 100% ethanol, e.g., to remove residual salts.

In some instances, the protein is released protein can be released, e.g., eluted, from the silica-containing surface, e.g., glass fiber membrane, spin filter, or magnetic beads. In some aspects, a small volume of elution buffer may be used to elute the proteins, for example, less than 10 µL, less than 20 µL, less than 50 µL, less than 100 µL, less than 500 µL, less than 1 mL or less than 5 mL. The buffer used for elution of the proteins may contain Tris, such as Tris having a pH of between or between about 6.0 and 10.0, e.g., between or between about 7.0 and 9.0, or has a pH that is or is about 8.0. In some aspects, the protein elution buffer can contain sodium dodecyl sulfate (SDS), such as 0.01-10.0%, e.g., 0.1-5.0%, or 0.5-1.0% SDS.

II. Kits for Isolation of Nucleic Acids and Proteins on a Silica-Containing Surface Also provided herein are kits containing a silica-containing surface, a high salt, low pH buffer, and instructions describing a method for use according to any of the embodiments described herein. In some embodiments, the kit further contains a guanidinium-containing buffer as described herein. In some embodiments, the kit may contain any of the compositions or combinations described herein. In some embodiments, the kit contains the compositions or combinations in a concentrated form. In some embodiments, the kit contains the compositions or combinations in solid form. In some embodiments, the kit contains the compositions or combinations in solution form. In some embodiments, the kit additionally contains solutions for dissolving or diluting the compositions and combinations prior to use. In some embodiments, the kit may additionally comprise solutions such as nucleic acid binding solutions, wash buffers, or elution solutions. Selected compositions including articles of manufacture thereof can also be provided as kits. Exemplary articles of manufacture include containers such as vials, bottles, jars, cans, and tubes.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

EXAMPLES

Example 1—DNA, RNA and Protein Isolation from Cultured Bacteria on Borosilicate Glass Spin Filter (with RNA/Protein Co-Isolation)

Cell Lysis: 1 mL of an overnight culture of *Escherichia coli* is centrifuged to pellet the cells. After removal of the supernatant, the cell pellet is resuspended in 400 µL of 1 M sodium thiocyanate (containing 1% beta-mercaptoethanol and protease inhibitors) and transferred to a 2 mL homogenization bead tube containing 0.1 mm glass beads (MO BIO catalog #13118-50). The cells are lysed by homogenization for 10 minutes and then pelleted by centrifugation at 10,000×g for 1 minute. 250 µL of the resulting clarified supernatant is transferred to a clean 2 mL collection tube.

DNA Isolation: 175 µL of 6 M guanidine thiocyanate is added to the 250 µL of supernatant and mixed thoroughly. The complete volume is loaded onto a borosilicate glass spin filter (MO BIO catalog #1200-50-SF) and centrifuged for 1 minute at 10,000×g to bind DNA to the glass membrane. The filtrate from this round of centrifugation is collected and set aside; the filtrate contains unbound RNA and protein. The membrane is washed with 500 µL, of 100% ethanol via centrifugation and then spun dry with another round of centrifugation. Captured, washed, DNA is eluted from the glass membrane with 100 µL, of PCR-grade water.

Simultaneous RNA & Protein Isolation: 350 µL, of RNA/Protein binding solution (51 mM citrate buffer, pH 3.4, 5 M NaCl) are added to the filtrate from the DNA isolation step above (approximately 425 µL), and the solution is mixed by vortexing for 10 seconds. The RNA and protein in this solution are bound to a fresh borosilicate glass spin filter via centrifugation as above and the filtrate is collected. The filtrate is combined with 500 µL, of 100% ethanol and passed through the same spin filter via centrifugation to bind low molecular weight RNAs (5S rRNA, transfer RNAs and small regulatory RNAs). To achieve sequential elution of bound RNA and proteins, two centrifugation steps are performed. To elute total cellular RNA, 100 µL, of DEPC-treated water is passed through the spin filter and collected. Total cellular proteins are eluted with 100 µL, of 10 mM Tris, pH 8.0 containing 1% sodium dodecyl sulfate.

This procedure is shown schematically in FIG. 1.

Example 2—Variation of RNA/Protein Binding Solution

A procedure analogous to that described in Example 1 was carried out with materials as shown in Table 1, wherein the RNA/Protein binding solution was varied to as shown in Table 1. Under Condition A, the RNA/Protein binding solution had both high salt concentration and low pH. Conditions B and C contained low pH and high salt, respectively, in the RNA/Protein binding solution, but not both.

TABLE 1

|  |  | A | B | C |
|---|---|---|---|---|
| Input | 1.8 ml *P. aeruginosa* | X | X | X |
| Lysis | 1M NaSCN, 400 µL | X | X | X |
|  | 4 µL beta-ME | X | X | X |
|  | 4 µL Protease Inhibitors | X | X | X |
| DNA Bind | 6M GuSCN, 250 µL | X | X | X |
| RNA/Protein Bind | Citric Acid/5M NaCl, 350 µL | X |  |  |
|  | Citric Acid, 350 µL |  | X |  |
|  | 5M NaCl, 350 µL |  |  | X |
| RNA Wash | 100% ethanol, 500 µL | X | X | X |
| RNA Elute | DEPC water | X | X | X |
| Protein Wash | 50% ethanol, 500 µL | X | X | X |
| Protein Elute | 1% SDS + 10 mM Tris, pH 8.0 | X | X | X |

Figure 2A:
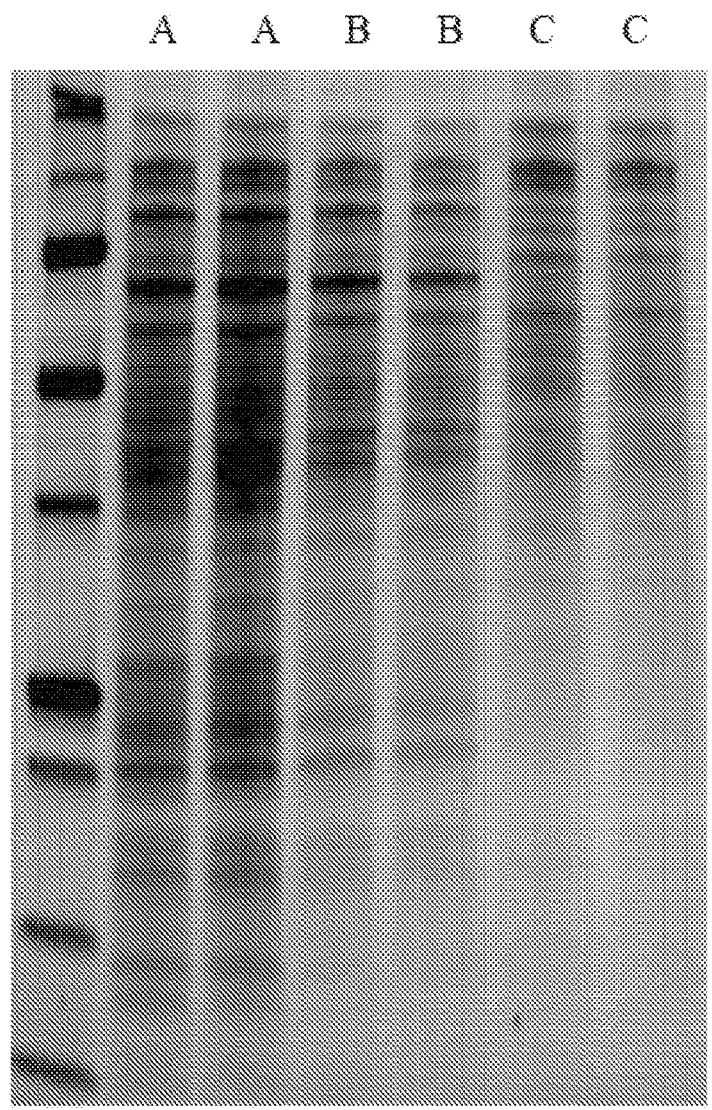
FIG. 2 is an SDS-Page protein gel (FIG. 2A) and RNA profile on agarose gel (FIG. 2B) for samples from *P. aeruginosa* under various extraction conditions (see Table 1)
Figure 2B:
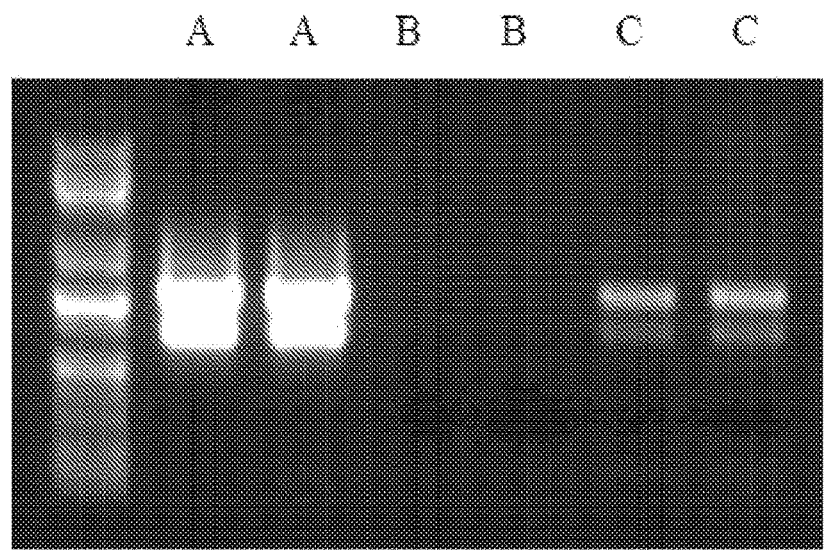

FIG. 2A shows SDS-Page protein gel of conditions A, B, and C, each in duplicate. FIG. 2B shows the RNA profile of conditions A, B, and C on an agarose gel. As shown in FIGS. 2A and 2B, substantial binding of both protein and RNA was observed under Condition A, but not under Conditions B or C.

Figure 3A:
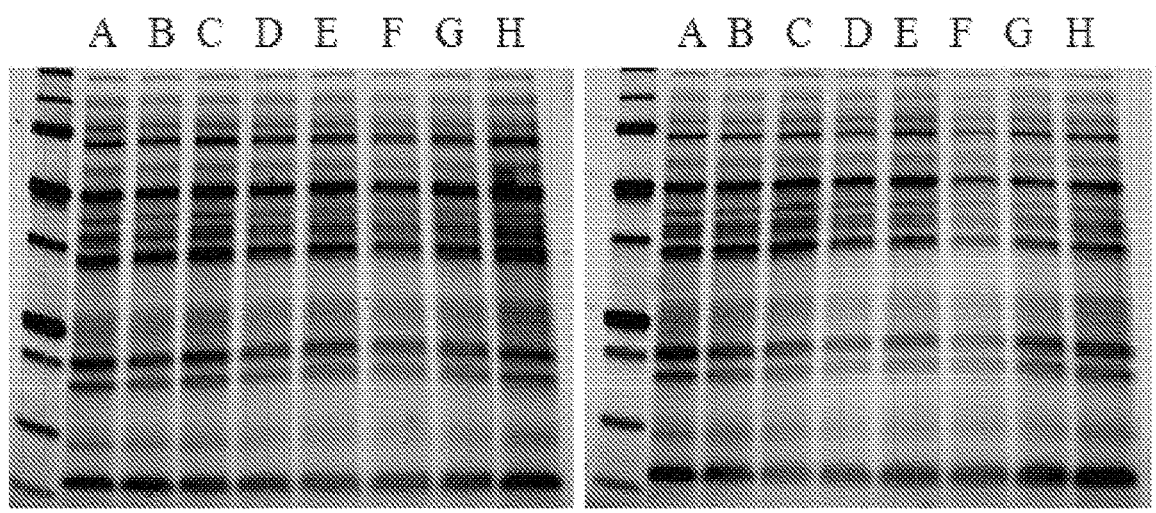
FIG. 3 is an SDS-Page protein gel (FIG. 3A) and RNA profile on agarose gel (FIG. 3B) for samples treated under various extraction conditions (see Table 2).
Figure 3B:
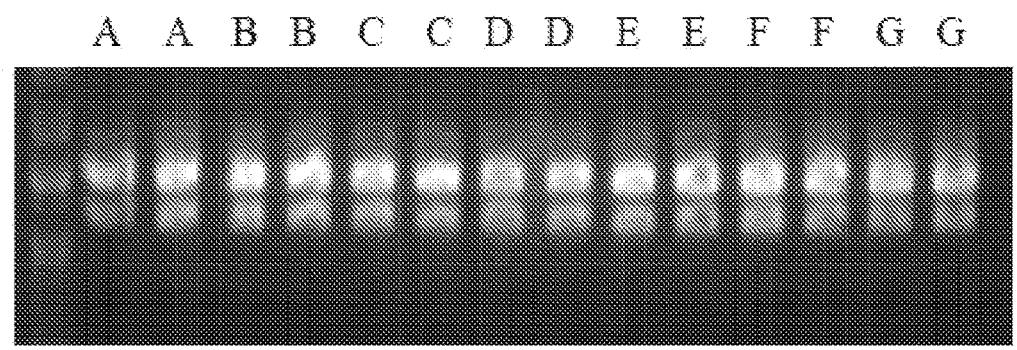

Additional RNA/Protein binding solutions were tested as indicated in Table 2. As shown in FIG. 3A (SDS-Page protein gel) and FIG. 3B (RNA profile on agarose gel), co-isolation of RNA and protein on borosilicate glass fibers was observed for a variety of high salt, low pH solutions.

TABLE 2

| Group | RNA/Protein Binding Solution |
|---|---|
| A | 51 mM citrate buffer, 5M NaCl, pH 3.54 |
| B | 10 mM citrate buffer, 5M NaCl, pH 3.5 |
| C | 200 mM citrate buffer, 5M NaCl, pH 3.5 |
| D | 50 mM glycine/HCl buffer, 5M NaCl, pH 3.5 |
| E | 200 mM glycine/HCl buffer, 5M NaCl, pH 3.5 |
| F | 5M NaCl in dilute HCl |
| G | 50 mM citrate/phosphate buffer, 5M NaCl, pH 3.5 |
| H | Control |

Figure 4A:
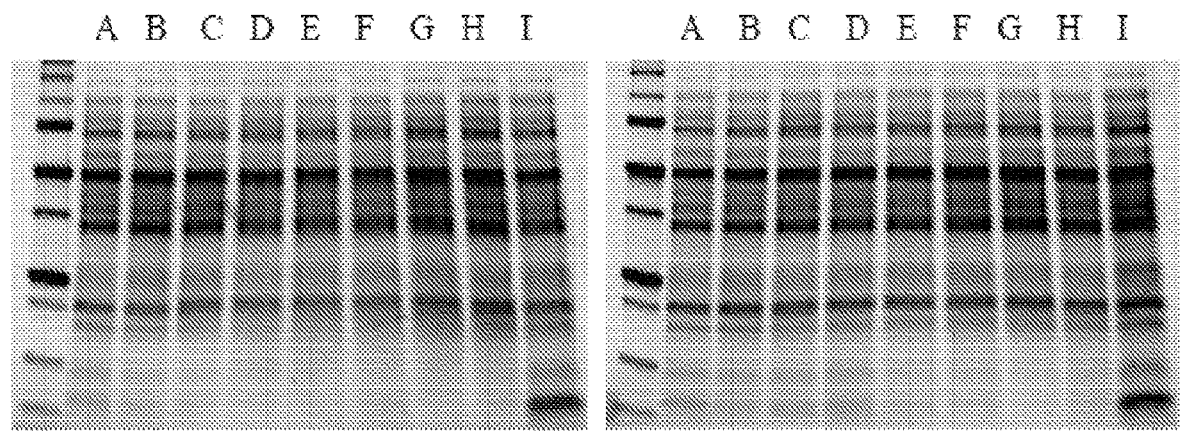
FIG. 4 is an SDS-Page protein gel (FIG. 4A) and RNA profile on agarose gel (FIG. 4B) for samples treated under various extraction conditions (see Table 3).
Figure 4B:
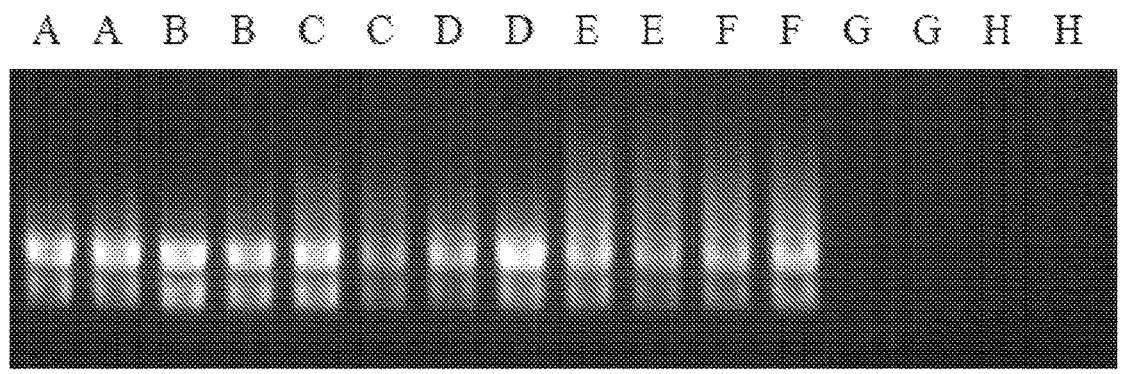

Further additional RNA/Protein binding solutions were tested as indicated in Table 3. As shown in FIG. 4A (SDS-Page protein gel) and FIG. 4B (RNA profile on agarose gel), co-isolation of RNA and protein on borosilicate glass fibers was observed for a variety of high salt, low pH solutions.

TABLE 3

| Group | RNA/Protein Binding Solution |
|---|---|
| A | 51 mM citrate buffer, 5M NaCl, pH 3.54 |
| B | 51 mM acetate buffer, 4M KCl, pH 3.41 |
| C | 155 mM acetate buffer, 4M KCl, pH 3.47 |
| D | 155 mM acetate buffer, 5M NaCl, pH 3.49 |
| E | 155 mM acetate buffer, 5M $NH_4Cl$, pH 3.41 |
| F | 5M NaCl in dilute HCl |
| G | 50 mM citrate buffer, 2.5M NaCl, 5% PEG-8000, pH 3.5 |
| H | 50 mM citrate buffer, 2.5M NaCl, 1.3% PEG-8000, pH 3.5 |
| I | Control |

Example 3—DNA, RNA and Protein Isolation from Cultured Bacteria on Silica-Coated Magnetic Beads (with RNA/Protein Co-Isolation)

Cell Lysis: 1 mL of an overnight culture of *Escherichia coli* was centrifuged to pellet the cells. After removal of the supernatant, the cell pellet was resuspended in 400 μL, of 1 M sodium thiocyanate (containing 1% beta-mercaptoethanol and protease inhibitors) and transferred to a 2 mL homogenization bead tube containing 0.1 mm glass beads (MO BIO catalog #13118-50). The cells were lysed by homogenization for 10 minutes and then pelleted by centrifugation at 10,000×g for 1 minute. 250 μL, of the resulting clarified supernatant was transferred to a clean 2 mL collection tube.

DNA Isolation: 175 μL, of 6 M guanidine thiocyanate was added to the 250 μL, of supernatant and mixed thoroughly. The complete volume was loaded onto 50 microliters of SwiftMag® (silica-coated magnetic beads, MO BIO), mixed for 5 minutes to bind DNA to the silica surface and collected on a magnet for 2 minutes. The supernatant from this step was collected and set aside; the filtrate contained unbound RNA and protein. The beads were washed with 500 μL, of 100% ethanol via magnetic concentration and then air dried to remove all ethanol. Captured, washed, DNA was eluted from the beads with 100 μL, of PCR-grade water.

Simultaneous RNA & Protein Isolation: 350 μL, of RNA/Protein binding solution (51 mM citrate buffer, pH 3.4, 5 M NaCl) were added to the filtrate from the DNA isolation step above (approximately 425 μL), and the solution was mixed by vortexing for 10 seconds. The RNA and protein in this solution were bound to a fresh 50 microliters of SwiftMag® via active mixing as above. To achieve sequential elution of bound RNA and proteins, two magnetic concentrations steps were performed. To elute total cellular RNA, 100 μL of DEPC-treated water was incubated with the SwiftMag® beads and collected. Total cellular proteins were eluted with 100 μL of 10 mM Tris, pH 8.0 containing 1% sodium dodecyl sulfate.

The conditions above and variations thereof are summarized in Table 4. Condition B was in the presence of borosilicate glass fiber filter (e.g., similar to the procedure described in Example 1), and Condition C was in the presence of SwiftMag® (silica-coated magnetic beads). Under Condition A, the samples were cleaned up by used of a desalting column; no silica-containing surface was used. This serves as control for total solubilized protein.

TABLE 4

| | | A | B | C |
|---|---|---|---|---|
| Input | 1.8 ml *P. aeruginosa* | X | X | X |
| Lysis | 1M NaSCN, 400 μL | X | X | X |
| | 4 μL beta-ME | X | X | X |
| | 4 μL Protease Inhibitors | X | X | X |
| DNA Bind | 6M GuSCN, 250 μL | X | X | X |
| RNA/Protein Bind | Citric Acid/5M NaCl, 350 μL | | X | X |
| | desalting column | | X | X |
| RNA Wash | 100% ethanol, 500 μL | | X | |
| | Ethanol | | X | |
| RNA Elute | DEPC water, 50 μL | | X | |
| Protein Wash | 50% ethanol, 500 μL | | X | X |
| Protein Elute | 1% SDS + 10 mM Tris, pH 8.0 | | X | X |
| | desalting column | X | | |

Figure 5:
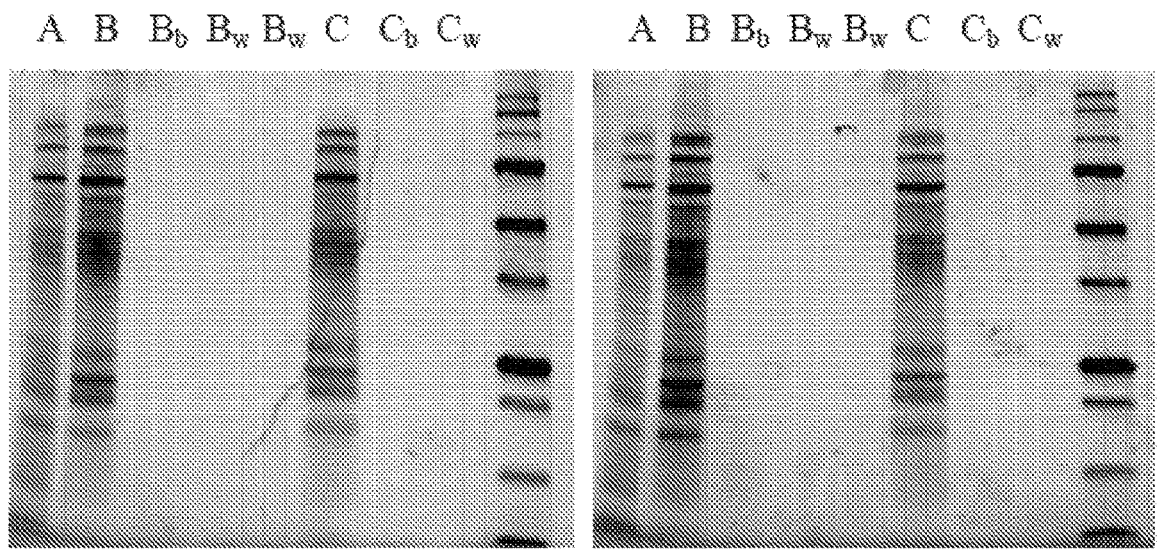
FIG. 5 is an SDS-Page protein gel for samples treated under various extraction conditions (see Table 4).

SDS-Page protein gel showing results for Conditions A, B, and C is shown in FIG. 5. For Conditions B and C, "b" denotes the bind, and "w" denotes the wash.

Example 4—Co-Isolation of Nucleic Acid and Protein

Cells are suspended in 1 M NaSCN. Cells are lysed via homogenization with 0.1 mm glass beads.

A sample containing cell lysate is mixed with an equal volume of high molarity guanidinium thiocyanate (GuSCN), such as 6 M GuSCN, and an acidic, high salt buffer such as a buffer containing 50 mM citrate (pH 3.5) and 5 M NaCl. The resulting solution is passed through a borosilicate glass fiber spin filter via centrifugation. DNA, RNA, and protein are bound to the filter. To elute the DNA and RNA from the spin filter, the filter is first washed with 100% ethanol to remove residual salts and then RNase-free water or TE is used to release the DNA and RNA from the glass fiber membrane.

The filter is then washed with 50% ethanol and proteins are eluted from the glass fiber membrane in the spin filter with a small volume (e.g., 100 μL) of Tris buffer, pH 8.0 containing 0.5-1.0% sodium dodecyl sulfate.

Figure 6:
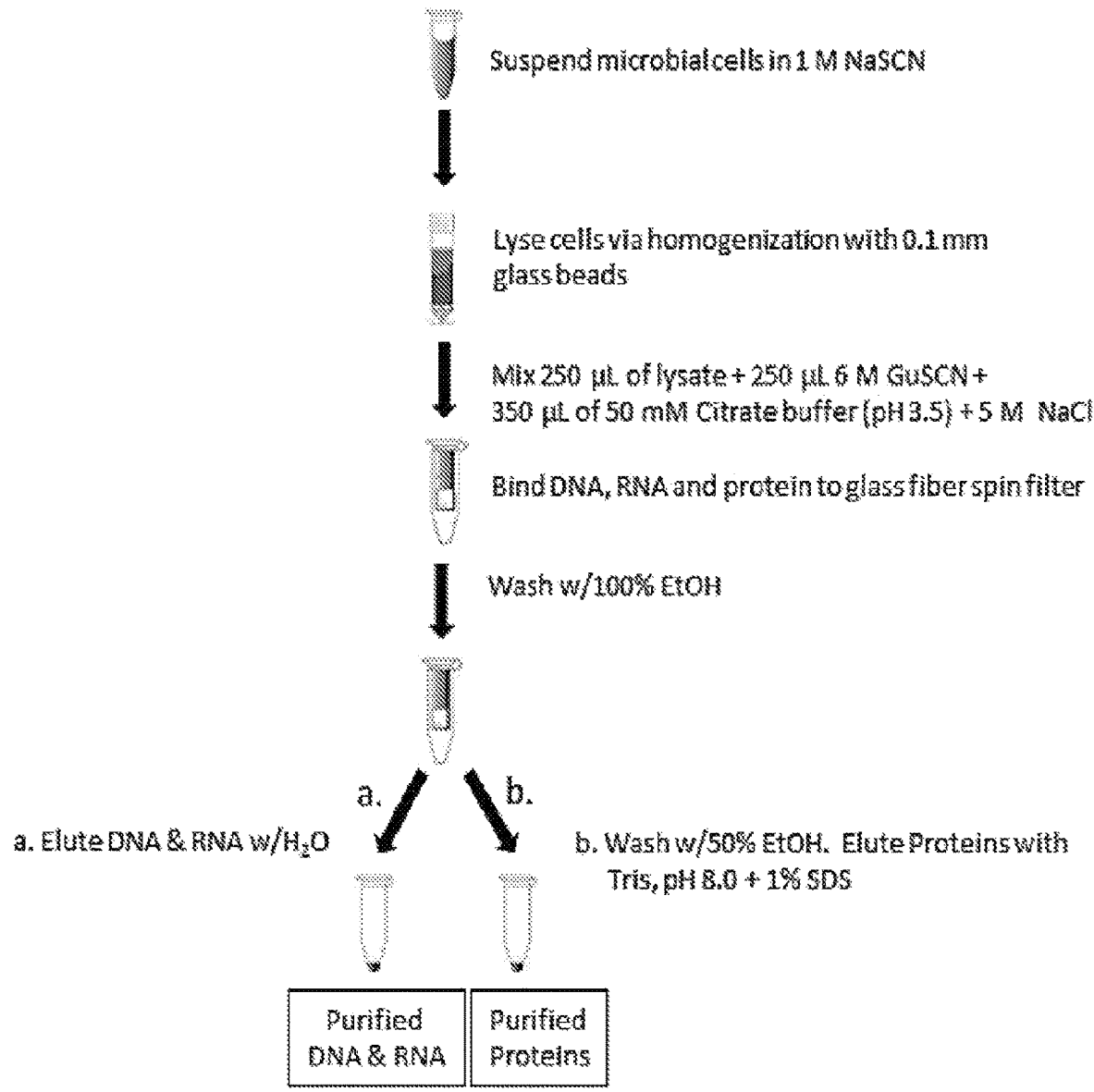
FIG. 6 is a schematic of an exemplary procedure in which DNA, RNA, and protein are co-isolated.

This procedure is shown schematically in FIG. 6.

The invention claimed is:

1. A method for the isolation of proteins from a sample, comprising:
    a) using a binding buffer to bind proteins from the sample with a silica-containing surface, wherein the binding buffer is a high salt, low pH buffer, and wherein the high salt, low pH buffer has a pH of less than or equal to 4.0 and a concentration of a salt of greater than 1 M; and
    b) separating the silica-containing surface comprising bound proteins from one or more other components of the sample.

2. The method of claim 1, wherein following step a), substantially all of the proteins comprised in the sample is bound to the silica-containing surface.

3. The method of claim 1, wherein the high salt, low pH buffer has a concentration of a chloride salt of greater than 2 M.

4. The method of claim 3, wherein the chloride salt comprises sodium, lithium, potassium, cesium, magnesium, calcium, strontium, zinc, copper, manganese, erbium, holmium, aluminum, or antimony.

5. The method of claim 3, wherein the chloride salt comprises sodium.

6. The method of claim 1, wherein prior to step a), the sample is contacted with a lysis buffer.

7. The method of claim 6, wherein the lysis buffer comprises 3M to 6M guanidinium thiocyanate.

8. The method of claim 1, wherein the silica-containing surface comprises borosilicate glass fibers, silicon dioxide glass fibers, or silica-coated magnetic beads.

9. The method of claim 8, wherein the one or more other components are biomolecules.

10. The method of claim 1, wherein the high salt, low pH buffer comprises citrate.

11. The method of claim 1, wherein the high salt, low pH buffer has a pH of less than or equal to 3.8.

12. The method of claim 1, wherein the high salt, low pH buffer has a pH in the range of 3.0 to 3.8.

13. The method of claim 2, wherein greater than about 80 wt. % of proteins from the sample are bound to the silica-containing surface.

14. The method of claim 2, wherein greater than about 90 wt. % of proteins from the sample are bound to the silica-containing surface.

15. The method of claim 1, wherein the high salt, low pH buffer has a salt concentration greater than 2M, greater than 3M, or greater than 4M.

16. The method of claim 1, wherein the high salt, low pH buffer has a salt concentration greater than 4 M and wherein the salt is an alkali metal salt.

17. The method according to claim 1, wherein the sample contains substantially no nucleic acids, optionally wherein the nucleic acids have been removed from the sample during a previous lysis procedure.

18. The method of claim 1, further comprising
c) performing a wash step to remove biomolecules or other components of the sample that may have bound nonspecifically to the silica-containing surface during step a); and/or
d) releasing the protein from the silica-containing surface.

19. The method of claim 1, wherein
the sample comprises RNA,
in step a), the silica-containing surface binds substantially all of the RNA and proteins comprised in the sample; and
in step b), the silica-containing surface comprising bound RNA and proteins is separated from one or more other components of the sample.

20. The method of claim 19, further comprising following step a):
centrifuging the silica-containing surface.

21. The method of claim 19, wherein the sample contains substantially no DNA.

22. The method of claim 19, wherein substantially no DNA is bound to the silica-containing surface.

23. The method of claim 19, wherein step b) further comprises binding substantially all DNA comprised in the sample to the silica-containing surface.

24. The method of claim 19, wherein the high salt, low pH buffer comprises a chloride salt at a concentration of chloride salt of greater than 2 M.

25. The method of claim 24, wherein the chloride salt comprises sodium, lithium, potassium, cesium, magnesium, calcium, strontium, zinc, copper, manganese, erbium, holmium, aluminum, or antimony.

26. The method of claim 24, wherein the chloride salt comprises sodium.

27. The method of claim 24, wherein the buffer comprises citrate.

28. The method of claim 1, wherein
the sample comprises DNA, RNA, proteins and one or more other components, prior to step a), the method further comprises:
i) contacting the sample with a first silica-containing surface;
ii) binding substantially all of the DNA comprised in the sample to the first silica-containing surface;
iii) separating the first silica-containing surface comprising bound DNA from a portion of the sample comprising RNA, proteins, and one or more other components;
iv) eluting the DNA from the first silica-containing surface;
in step a), contacting the portion of the sample comprising RNA, proteins, and one or more other components with a second silica-containing surface, whereby the second silica-containing surface binds substantially all of the RNA and proteins comprised in the portion of the sample comprising RNA, proteins, and one or more other components; and
in step b), separating the second silica-containing surface comprising bound RNA and proteins from the one or more other components.

29. The method of claim 28, further comprising following steps i) and a):
centrifuging the first and second silica-containing surface.

30. The method of claim 28, wherein substantially no RNA or proteins are bound to the first silica-containing surface in steps i) iv).

31. The method of claim 28, wherein in step i), the sample comprises a first buffer comprising guanidinium thiocyanate, and wherein the sample is substantially free of organic solvent.

32. The method of claim 31, wherein a concentration of guanidinium thiocyanate in the first buffer is greater than 1 M.

33. The method of claim 28, wherein in step a) the high salt, low pH buffer comprises a chloride salt at a concentration of greater than 2 M.

34. The method of claim 33, wherein the chloride salt comprises sodium, lithium, potassium, cesium, magnesium, calcium, strontium, zinc, copper, manganese, erbium, holmium, aluminum, or antimony.

35. The method of claim 33, wherein the chloride salt comprises sodium.

36. The method of claim 33, wherein the high salt, low pH buffer comprises citrate.

37. The method of claim 33, further comprising after step iv), combining the portion of the sample comprising RNA, proteins, and one or more other components in the first buffer with the high salt, low pH buffer.

38. The method of claim 37, further comprising eluting the RNA and proteins from the second silica-containing surface.

39. The method of claim 38, wherein the RNA and protein are eluted sequentially.

40. The method of claim 38, wherein the RNA is eluted with RNase-free water or TE buffer.

41. The method of claim 38, wherein the protein is eluted with a buffer comprising Tris with a pH of about 8.0 and 0.5-1% sodium dodecyl sulfate.

42. The method of claim 23, wherein the RNA and DNA are simultaneously eluted from the silica-containing surface.

43. The method of claim 23, wherein the DNA is eluted with DNase/RNase-free water, TE buffer, or buffer comprising Tris with a pH of about 8.0.

44. The method according to claim 28, wherein the first silica-containing surface in step i) is the same as the second silica-containing surface in step a).

45. The method according to claim 28, wherein the first silica-containing surface in step i) is different from the second silica-containing surface in step a).

46. The method of claim 1, wherein the method does not comprise the use of phenol.

\* \* \* \* \*

UNITED STATES PATENT AND TRADEMARK OFFICE
CERTIFICATE OF CORRECTION

PATENT NO. : 11,242,518 B2
APPLICATION NO. : 15/757330
DATED : February 8, 2022
INVENTOR(S) : Heather Callahan et al.

Page 1 of 1

It is certified that error appears in the above-identified patent and that said Letters Patent is hereby corrected as shown below:

In the Claims

Column 25, Claim 17, Lines 28-29:
"wherein the nucleic acids" should read: -- wherein nucleic acids --.

Signed and Sealed this
Ninth Day of January, 2024

Katherine Kelly Vidal
*Director of the United States Patent and Trademark Office*